United States Patent
Pendharkar et al.

(10) Patent No.: US 7,718,412 B2
(45) Date of Patent: May 18, 2010

(54) HEMOSTATIC COMPOSITIONS CONTAINING STERILE THROMBIN

(75) Inventors: Sanyog M. Pendharkar, Edison, NJ (US); Anne J. Gorman, Hightstown, NJ (US)

(73) Assignee: Ethicon, Inc., Somerville, NJ (US)

( * ) Notice: Subject to any disclaimer, the term of this patent is extended or adjusted under 35 U.S.C. 154(b) by 405 days.

(21) Appl. No.: 10/567,388

(22) PCT Filed: Jul. 23, 2004

(86) PCT No.: PCT/US2004/023765

§ 371 (c)(1), (2), (4) Date: Feb. 7, 2006

(87) PCT Pub. No.: WO2005/016256

PCT Pub. Date: Feb. 24, 2005

(65) Prior Publication Data

US 2006/0204490 A1 Sep. 14, 2006

Related U.S. Application Data

(60) Provisional application No. 60/493,116, filed on Aug. 7, 2003.

(51) Int. Cl.
*A61K 38/48* (2006.01)
*C12N 9/74* (2006.01)
*C12Q 1/56* (2006.01)

(52) U.S. Cl. ............ 435/214; 435/214; 435/13

(58) Field of Classification Search ........... None
See application file for complete search history.

(56) References Cited

U.S. PATENT DOCUMENTS

| | | |
|---|---|---|
| 2,507,244 A | 5/1950 | Correll |
| 3,743,140 A | 7/1973 | Sauerbrey |
| 4,655,211 A | 4/1987 | Sakamoto et al. |
| 4,891,359 A | 1/1990 | Saferstein et al. |
| 5,143,838 A | 9/1992 | Kraus et al. |
| 5,595,735 A | 1/1997 | Saferstein et al. |
| 5,677,284 A | 10/1997 | Li |
| 5,733,572 A | 3/1998 | Unger et al. |
| 5,908,054 A | 6/1999 | Safabash et al. |
| 6,045,570 A | 4/2000 | Epstein et al. |
| 6,063,061 A | 5/2000 | Wallace et al. |
| 6,066,325 A | 5/2000 | Wallace et al. |
| 6,120,751 A | 9/2000 | Unger |
| 6,432,415 B1 | 8/2002 | Osborne et al. |
| 6,566,345 B2 | 5/2003 | Miller et al. |
| 6,605,066 B1 | 8/2003 | Gravagna et al. |
| 7,109,163 B2 | 9/2006 | Pendharkar et al. |
| 2002/0042378 A1 | 4/2002 | Reich et al. |
| 2002/0114775 A1 | 8/2002 | Pathak |
| 2002/0193448 A1 | 12/2002 | Wallace et al. |
| 2003/0028140 A1 | 2/2003 | Greff |
| 2003/0064109 A1 | 4/2003 | Qian et al. |
| 2003/0077272 A1 | 4/2003 | Pathak |
| 2003/0129183 A1 | 7/2003 | Spillert et al. |
| 2005/0037088 A1 | 2/2005 | Pendharkar et al. |
| 2006/0127488 A1 | 6/2006 | Pendharkar et al. |

FOREIGN PATENT DOCUMENTS

| | | |
|---|---|---|
| EP | 0740528 B1 | 3/2003 |
| EP | 0927053 B1 | 4/2003 |
| EP | 1 559 438 | 8/2005 |
| GB | 1 018 647 | 1/1996 |
| JP | 62228009 A | 10/1987 |
| WO | 94/23788 | 10/1994 |
| WO | WO 98/08550 A1 | 3/1998 |
| WO | 00/033894 | 6/2000 |
| WO | WO 00/76533 A1 | 12/2000 |
| WO | 01/28603 | 4/2001 |
| WO | WO 01/97826 A2 | 12/2001 |
| WO | WO 01/97873 A2 | 12/2001 |
| WO | WO 02/072128 A1 | 9/2002 |
| WO | WO 03/007845 A1 | 1/2003 |
| WO | WO 03/055531 A2 | 7/2003 |
| WO | WO 2005/016256 A | 2/2005 |
| WO | WO 2005/016257 A | 2/2005 |

OTHER PUBLICATIONS

Sakurabayashi, "Clinical Evaluation of New Hemostatic Agent for Hemostasis from Biopsy Wounds in the Liver" Gastroenterological Endoscopy, vol. 30(1), (Oct. 1988) pp. 2256.

(Continued)

*Primary Examiner*—David M. Naff
*Assistant Examiner*—Deborah K. Ware
(74) *Attorney, Agent, or Firm*—Roberts Mlotkowski Safran & Cole, P.C.

(57) ABSTRACT

The present invention includes sterilized hemostatic compositions that contain a continuous, biocompatible liquid phase having a solid phase of particles of a biocompatible polymer suitable for use in hemostasis and that is substantially insoluble in the liquid phase, and sterile thrombin, each of which is substantially homogenously dispersed throughout the continuous liquid phase, and methods for making such compositions.

14 Claims, No Drawings

OTHER PUBLICATIONS

Wikipedia, the free encyclopedia. Hypertext address: en.wikipedia.org/wiki/Foaming_agent (Accessed on Apr. 13, 2007).

Wikipedia article (downloaded Nov. 9, 2007): 'Foam '; website: http.//en.wikipedia.org/wiki/foam.

Merriam-Webster Entry (downloaded Nov. 9, 2007): "Foam ": website: http//www.merriam-webster.com/dictionary/foam.

International Search Report dated Dec. 12, 2005 for corresponding U.S. Appl. No. PCT/US04/23799.

International Search Report dated Jul. 12, 2005 for corresponding U.S. Appl. No. PCT/US04/23765.

HEMOSTATIC COMPOSITIONS CONTAINING STERILE THROMBIN

CROSS REFERENCE TO RELATED APPLICATIONS

This application is a National Stage application under 35 U.S.C. 371 of PCT/US2004/023765, filed Jul. 23, 2004, which claims priority from U.S. Provisional Application Ser. No. 60/493,116, filed Aug. 7, 2003. Benefit of U.S. Ser. No. 10/896,647, filed on Jul. 21, 2004 is also claimed.

FIELD OF THE INVENTION

The present invention relates to hemostatic compositions containing sterile thrombin and to methods of making such hemostatic compositions.

BACKGROUND OF THE INVENTION

Gelatin-based hemostats, both in solid sponge or powder form, are commercially available and are used in surgical procedures. Gelatin powder, when mixed with fluid, can be prepared in various forms depending on the contemplated end-use and the ratio of fluid to powder. For example, where higher concentrations of fluid are employed, a paste or slurry that is useful as a flowable, extrudable and injectable hemostat may be prepared for use in diffuse bleeding, particularly from uneven surfaces or hard to reach areas. Such conventional slurries are prepared at the point of use by mechanical agitation and mixing of the powder and liquid to provide uniformity of the composition. The paste then is placed into a delivery means or applicator, e.g. a syringe, and applied to the wound. In other cases, moldable compositions may be prepared with lower amounts of fluid and molded or packed to form a dressing for use on external wounds. Gelatin powders are sterilized prior to preparing such compositions but mixing of the powders and fluids may compromise the sterility of the hemostatic composition due to handling of the materials at the site of use, or in general by exposure to the environment for relatively extended periods of time during mixing and the like.

Thrombin that is not terminally sterilized is known to be used in combination with such hemostatic compositions. Proteins such as thrombin are prepared aseptically and thus there is a risk that nonsterilized proteins such as thrombin, when used in hemostatic compositions, may compromise the sterility of the previously-sterilized materials, such as sterilized gelatin powder. However, as thrombin is known to be denatured by exposure to sterilizing condition such as ionizing radiation conventionally used to sterilize the powders, which denaturing destroys all enzymatic activity of the thrombin, thrombin has not been reported to be incorporated into the hemostatic compositions and then terminally sterilized prior to use to ensure a sterile composition. In fact, when thrombin is used in conventional hemostatic compositions, nonsterilized thrombin is added after sterilization of hemostatic composition.

It would be desirable if a sterile hemostatic composition containing active sterile thrombin was available to the surgeon at the point of use without need for preparation, e.g. without having to add thrombin prior to use. The compositions of the present invention fulfill that need.

SUMMARY OF THE INVENTION

The present invention is directed to sterilized hemostatic compositions comprising a continuous, biocompatible liquid phase, a solid phase comprising porous or non-porous particles of a biocompatible polymer suitable for use in hemostasis and which are substantially insoluble in the liquid phase, and sterile thrombin. The continuous liquid phase comprises the solid particulate phase and sterile thrombin substantially homogenously dispersed there through. The ratio of the liquid phase, the solid particulate phase and thrombin is effective to provide the composition with hemostatic properties, both prior to and after sterilization. Sterile compositions of the present invention may be prepared well in advance of the time of use while maintaining thrombin enzymatic activity even after being subjected to sterilizing radiation. The present invention also includes methods of making the hemostatic compositions.

DETAILED DESCRIPTION OF THE INVENTION

Sterilized compositions of the present invention contain solid, porous or non-porous particles of a biocompatible polymer suitable for use in hemostasis, a biocompatible liquid and sterile thrombin as its three primary components. Particles, liquid and thrombin are combined and mixed under conditions effective to provide a substantially homogeneous hemostatic composition comprising a continuous liquid phase comprising the thrombin and having the solid polymer particles homogenously dispersed there through. The amount and average diameter of particles contained in the composition and the relative amounts of the solid, liquid and thrombin is effective to provide the composition with hemostatic and physical properties, as described herein below.

Compositions of the present invention may be prepared and sterilized by ionizing irradiation well in advance of the time of their intended use, while maintaining thrombin enzymatic activity effective to improve hemostasis of the composition when compared to a similar composition containing no thrombin or where the thrombin activity has been substantially diminished such that it no longer enhances hemostasis. This is particularly surprising given that it is known in the art that thrombin is denatured when exposed to irradiation of the type used to sterilize conventional hemostatic compositions containing, for example, gelatin powder. Denaturing causes the thrombin to lose its enzymatic activity. The compositions further may include additives to facilitate the preparation of the composition, enhance physical and mechanical properties, enhance the hemostatic properties of the composition or provide antimicrobial properties.

As used herein, "continuous" and "discontinuous" are used in the ordinary meaning of those words in the context of standard nomenclature used to define and describe dispersions.

As used herein, "substantially homogenous" denotes that physical state of the compositions or pastes where the solid particles are uniformly dispersed throughout the continuous liquid phase such that the ratio of solid:liquid and the density of any portion or cross-section of the composition or paste are substantially the same.

As used herein, "sterile" means substantially free of living germs and/or microorganisms and as further recognized and described by governmental standards pertaining to compositions and medical devices described and claimed herein.

As used herein, "hemostatic", or "hemostatic properties", means the ability to stop or minimize bleeding, as one skilled in the art of hemostasis would understand those terms to mean, as further exemplified in the examples of the specification.

A variety of biocompatible natural, semi-synthetic or synthetic polymers may be used to prepare the solid particles used in compositions of the present invention. The polymer selected must be substantially insoluble in the liquid chosen for the particular composition. Preferably, water-insoluble biodegradable polymers that provide mechanical, chemical and/or biological hemostatic activity are used. Polymers that may be used include, without limitation, proteins and polysaccharides. Polysaccharides that may be used include oxidized cellulose, chitosan, chitin, alginate, oxidized alginate and oxidized starch. The biocompatible polymer used to prepare the particles preferably is a cross-linked or denatured protein, such as gelatin, collagen, fibrinogen or fibronectin. A preferred gelatin powder is a partially cross-linked gelatin powder prepared by milling gelatin sponge into particles having an average diameter of from about 40 microns to about 1200 microns, more preferably from about 100 microns to about 1000 microns, as determined by laser diffraction.

Sterile compositions of the present invention comprise a continuous liquid phase in which the sterile thrombin and solid particles are dispersed. Depending upon the particular medical device and use thereof, the liquid may be aqueous or non-aqueous. Preferably, the liquid phase is aqueous. Aqueous liquids may include, without limitation, biocompatible aqueous solutions, such as calcium chloride and saline. More preferably, the liquid phase comprises saline. The liquid phase and solid particulate phase are present in relative amounts effective to provide a composition, for example a paste, or slurry, suitable for use in providing hemostasis. In certain embodiments, the weight ratio of solid particles to liquid generally is from about 1:1 to about 1:12, or from about 1:3 to about 1:8 or even about 1:5.

Compositions of the present invention include compositions described herein that are sterile, in that they have been irradiated with a level of, e.g. ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

As noted herein, thrombin, in an aqueous solution, has been found to lose all procoagulant activity when exposed to sterilization irradiation. In contrast, sterile thrombin contained in compositions of the present invention retain enzymatic activity sufficient to provide hemostatic properties to compositions of the present invention after being subjected to irradiation sufficient to provide sterilized compositions disclosed herein. Sterile thrombin in compositions of the present invention may lose only about 20 percent of its original enzymatic activity prior to sterilization. In certain embodiments of the present invention, the sterile thrombin exhibited a loss of enzymatic activity of not more than about 40% of its original enzymatic activity prior to sterilization, while maintaining all of its hemostatic activity after sterilization, when formulated in compositions according to this invention. While bovine thrombin is exemplified herein, human-derived thrombin, as described in U.S. Pat. No. 5,143,838, also may be used in compositions of the present invention. The discovery that thrombin will maintain activity after being exposed to sterilizing radiation as described above is particularly surprising given the previous teachings of the art that would strongly suggest that if thrombin were to be used in hemostatic compositions it should be added after sterilization of the composition, not prior to sterilization.

The hemostatic compositions may further comprise effective amounts of one or more additives or compounds including, but not limited to, antimicrobial agents, surfactants, antioxidants, humectants, wetting agents, lubricants, thickeners, diluents, irradiation stabilizers, e.g. radical scavengers, plasticizers, and stabilizers. For example, glycerol may be added to enhance the extrudability or injectability of the composition. When utilized, glycerol may be present in the compositions at from about 0% to about 20% by weight, based on the weight of the liquid phase. Preferably, the composition may comprise from about 1% to about 10% by weight of glycerol, based on the weight of the liquid phase. More preferably, the compositions may comprise from about 1% to about 5% by weight of glycerol, based on the weight of the liquid phase.

In addition, quaternary amines may be used to provide enhanced properties to the compositions. For example, benzalkonium chloride, Polybrene or Onamer M may be used at levels up to about 1 percent by weight, based on the weight of the liquid phase. Preferably, benzalkonium chloride is used at levels of from about 0.001% to about 0.01% by weight, based on the weight of the liquid phase. More preferably, the compositions may comprise from about 0.002 to about 0.006% by weight benzalkonium chloride, based on the weight of the liquid phase. It is believed that the quaternary amines may serve multiple functions, acting as an antimicrobial agent, a foaming agent, a radical scavenger and as a heparin neutralizer.

Such hemostatic compositions may further comprise heparin neutralizers, additional procoagulants or hemostatic agents, such as fibrinogen, fibrin, Factor Xa, or Factor VIIa. By "effective amount", it is meant that amount necessary to provide to the compositions those properties for which the additive is being added. The effective amount also is limited by the maximum amount that may be added without causing detrimental biological affects.

Medical devices in which the hemostatic compositions of the present invention may be utilized include any device currently being used to apply a flowable or injectable hemostatic paste or slurry to a site, or wound, requiring hemostasis. The site requiring hemostasis may be the result of an injury or a surgical procedure. Examples of devices or applicators include syringes such as Becton Dickinson or Monoject luer syringes. Other devices are disclosed in detail in U.S. Pat. No. 6,045,570, the contents of which are incorporated by reference in their entirety.

In one embodiment for making compositions of the invention, a substantially homogenous paste is prepared by mixing the particles with the liquid to form a uniform paste. The liquid includes the thrombin and may include effective amounts of other additives dissolved therein as described above. Mixing may be accomplished by extrusion or by mixing in a confined space under conditions effective to provide a uniform dispersion of the solid particles in the liquid phase.

Alternately, a mixer, e.g. a double planetary mixer, may be utilized in making compositions of the present invention. The liquid containing the thrombin is added to the mixer. The liquid may include effective amounts of additives dissolved therein prior to addition of particles to the solution. For example, a saline solution containing thrombin, glycerol and benzalkonium chloride may be prepared and then added to the mixer. The solid particles are added to the mixer over time with continuous mixing until all ingredients have been added. The mixing is continued until such time as a substantially homogenous composition is formed containing the solid particles uniformly dispersed throughout the continuous liquid phase.

The hemostatic compositions prepared as above are sterilized to provide sterile compositions comprising sterile thrombin. In some embodiments the compositions are transferred into a medical device as described above and the device containing the hemostatic composition is sterilized, preferably by ionizing radiation. More preferably, sterilization is by gamma irradiation as exemplified herein.

While the following examples demonstrate certain embodiments of the invention, they are not to be interpreted as limiting the scope of the invention, but rather as contributing to a complete description of the invention.

Example 1

Two vials of lyophilized Bovine thrombin (20,000 units Thrombogen JJMI) were reconstituted in 20 ml of saline to provide a working solution of 1,000 units/ml. Clotting activity was measured in an in vitro test as described in Example 2. One vial of this material was stored at 4-8° C. and the clotting activity measured at day 1, day 8 and day 30, respectively. The second vial was sterilized by gamma irradiation (25 kGy) and the clotting activity measured as above. The unsterilized and sterilized samples were designated samples 1a and 1b, respectively. Both sterilized and unsterilized samples were stored at 4-8° C. between measurements.

Another 2 vials of 20,000 units of lyophilized bovine thrombin were reconstituted in saline containing 0.005% benzalkonium chloride and 5% glycerol. One vial was stored at. 4-8° C. and the clotting activity was measured at day 0, day 1, day 8 and day 30. The second vial was sterilized by gamma irradiation (25 kGy) and the clotting activity measured as above. In between measurements both the sterilized and unsterilized samples were stored at 4-8° C. The unsterilized and sterilized samples were designated samples 1c and 1d, respectively.

Several samples of gelatin paste containing the thrombin noted above were prepared by mixing 1 gram of Surgifoam gelatin powder with 5 ml of thrombin solution. The resulting paste was loaded into a 10 cc syringe. Samples were then either sterilized at 25 kGy followed by storage at 4-8° C., or stored unsterilized at 4-8° C. Samples so prepared are designated and identified below.

Sample 1e=1 g Surgifoam® powder plus 5 ml of sample 1a; Sterilized

Sample 1f=1 g Surgifoam® powder plus 5 ml of sample 1c; Unsterilized

Sample 1g=1 g Surgifoam® powder plus 5 ml of sample 1c; Sterilized

Example 2

Measurement of Thrombin activity by an in vitro coagulation test in a Fibrometer instrument (BBL)

Method: Serial dilutions of test sample containing thrombin were prepared in Veronal buffer pH 7.2. 0.2 ml of pooled normal plasma (Citrol Level 1 control plasma-Dade Diagnostics) was warmed to 37° C. in the fibrometer incubator block. 0.1 ml of pre-warmed sample dilution was added to the plasma and the timer started simultaneously. The time to clot formation was recorded. All samples were tested in duplicate and an average clotting time calculated. Data was graphed as the $\log_{10}$ dilution vs. $\log_{10}$ clotting time and a regression analysis performed. Freshly prepared thrombin was considered to have 100% activity and all other samples were calculated as a percentage of the activity relative to the freshly prepared thrombin. Results are presented in Table 1 and Table 2.

TABLE 1

Effect of Storage time on Thrombin Activity: Stabilization by Formulated Gelatin Paste

| Storage Solution | Percent Loss in Thrombin Activity | | | |
|---|---|---|---|---|
| (Stored at 6° C.) | Time 0 | Day 1 | Day 8 | Day 30 |
| 1a | 0 | 0 | 53.3 | 90.8 |
| 1c | 0 | NA | 41.1 | 82.9 |
| 1f | 0 | 0 | 0.8 | 0 |

TABLE 2

Effect of Gamma Irradiation on Thrombin Activity: Stabilization by Formulated Gelatin paste

| Media for Sterilized Thrombin * Samples (5 ml/g gelatin powder—25 kGy Dose) | % Loss in Thrombin Activity Day 6 |
|---|---|
| 1b | 100 |
| 1d | 96.0 |
| 1e | 72.6 |
| 1g | 79.2 |

TABLE 3

In vivo Hemostasis Performance of Pre-filled Thrombin/Gelatin Paste

| TIME: SAMPLE | Number of Compressions | Time to Hemostasis (mins:secs) |
|---|---|---|
| Day 0: 1f | 1 | 0:30 |
| Day 42: 1f | 1 | 0:30 |
| Day 42: 1f | 1 | 0:30 |
| Day 42: 1g | 1 | 0:30 |
| Day 42: 1g | 1 | 0:30 |

Example 3

Sterilization of Frozen Thrombin by Gelatin Paste

One vial of 20,000 units of lyophilized bovine thrombin (Thrombogen JJMI) was reconstituted in saline containing 0.005% BAK and 5% glycerol. 1 gram of Surgifoam® powder was mixed with 5 ml of thrombin-containing saline solution. The resulting paste was loaded into a 10 ml syringe. The sample were frozen at −20° C. and sterilized by gamma irradiation at a dose of 25 kG. Thrombin clotting activity was measures as described in Example 2. It was noted that only 42 percent of thrombin activity was lost due to sterilization.

We claim:

1. A method for making a sterile hemostatic composition, comprising:

providing a biocompatible liquid having thrombin dissolved therein, combining said liquid comprising said thrombin with particles of a biocompatible polymer suitable for use in hemostasis and which is substantially insoluble in said liquid, mixing said liquid comprising said thrombin and said particles under conditions effective to form a continuous liquid phase comprising said thrombin and said particles substantially homogenously dispersed there through, thereby forming a substantially homogeneous hemostatic composition; and irradiating said substantially homogeneous hemostatic composition with an amount of ionizing radiation and for a time effective to provide a sterile, substantially homogeneous hemostatic composition, wherein the ratio of said continuous liquid phase and said particles is effective to provide said composition with hemostatic properties and wherein said thrombin maintains at least a portion of its enzymatic activity.

2. The method of claim 1 wherein said liquid phase comprises saline.

3. The method of claim 2 wherein said biocompatible polymer is selected from the group consisting of proteins and polysaccharides.

4. The method of claim 2 wherein said protein is selected from the group consisting of gelatin, collagen, fibrinogen and fibronectin.

5. The method of claim 3 wherein said protein comprises gelatin.

6. The method of claim 1 wherein said sterile thrombin has lost not more than about 20 percent of the enzymatic activity it possessed prior to sterilization.

7. A sterile hemostatic composition in liquid form prepared by the method of claim 1, comprising:

a continuous, biocompatible liquid phase comprising sterile thrombin; and a solid phase comprising particles of a biocompatible polymer suitable for use in hemostasis and which is substantially insoluble in said liquid phase, said continuous liquid phase comprising said solid phase and said sterile thrombin substantially homogenously dispersed there through, wherein the ratio of said liquid phase and said solid phase is effective to provide said composition with hemostatic properties and said sterile thrombin comprises enzymatic activity.

8. The method of claim 7 wherein said sterile thrombin has lost not more than about 20 percent of the enzymatic activity it possessed prior to sterilization.

9. The sterile hemostatic composition of claim 8 wherein said liquid phase comprises saline.

10. The sterile hemostatic composition of claim 9 wherein said biocompatible polymer is selected from the group consisting of proteins and polysaccharides.

11. The sterile hemostatic composition of claim 10 wherein said protein is selected from the group consisting of gelatin, collagen, fibrinogen and fibronectin.

12. The sterile hemostatic composition of claim 11 wherein said protein comprises gelatin.

13. The sterile hemostatic composition of claim 8 wherein said sterile thrombin has lost not more than about 20 percent of the enzymatic activity it possessed prior to sterilization.

14. The sterile hemostatic composition of claim 8 wherein said sterile thrombin has lost not more than about 40 percent of the enzymatic activity it possessed prior to sterilization.

* * * * *